(12) United States Patent
Pruyne

(10) Patent No.: US 10,105,109 B2
(45) Date of Patent: Oct. 23, 2018

(54) CUSHION RETAINER

(71) Applicant: Carestream Health, Inc., Rochester, NY (US)

(72) Inventor: Adam D. Pruyne, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 365 days.

(21) Appl. No.: 14/936,773

(22) Filed: Nov. 10, 2015

(65) Prior Publication Data

US 2016/0228073 A1 Aug. 11, 2016

Related U.S. Application Data

(60) Provisional application No. 62/112,190, filed on Feb. 5, 2015.

(51) Int. Cl.
| | |
|---|---|
| *A47C 31/00* | (2006.01) |
| *A47C 27/00* | (2006.01) |
| *A61B 6/03* | (2006.01) |
| *H01F 7/02* | (2006.01) |
| *A61B 6/04* | (2006.01) |
| *A61B 6/00* | (2006.01) |

(52) U.S. Cl.
CPC ............ *A61B 6/032* (2013.01); *A47C 31/003* (2013.01); *A61B 6/04* (2013.01); *A61B 6/50* (2013.01); *H01F 7/0252* (2013.01); *Y10S 5/906* (2013.01)

(58) Field of Classification Search
CPC . Y10S 5/906; A47C 31/003; A47G 2200/106; A61N 2/00; A61N 2/002; A61N 2/004; A61N 2/006; A61N 2/008; A61N 2/02; A61N 2/06

USPC .......................................... 5/693, 906; 600/9
See application file for complete search history.

(56) References Cited

U.S. PATENT DOCUMENTS

| | | | | | |
|---|---|---|---|---|---|
| 3,123,935 | A | * | 3/1964 | Williams | A47B 13/16 108/116 |
| 4,046,365 | A | * | 9/1977 | Dungan | A61G 13/125 5/649 |
| 4,360,193 | A | * | 11/1982 | Mitchell | A61G 13/12 5/649 |
| 4,407,687 | A | * | 10/1983 | Mitchell | A61G 13/12 5/649 |
| 4,905,712 | A | * | 3/1990 | Bowlin | A61F 5/05883 128/870 |
| 5,551,110 | A | * | 9/1996 | Armstrong | A47G 9/1009 135/121 |
| 6,824,511 | B1 | * | 11/2004 | Bell | A61B 17/02 600/227 |
| 7,028,352 | B2 | * | 4/2006 | Kramer | A61G 7/05 428/430 |
| 7,222,377 | B2 | * | 5/2007 | Kramer | A61G 7/05 5/425 |

(Continued)

*Primary Examiner* — Robert G Santos

(57) ABSTRACT

A cushion comprises a magnet disposed therewithin proximate one or both of two major surfaces in the cushion. A medical diagnostic device comprises a contact surface wherein a part of the patient's body contacts the diagnostic device. The contact surface is configured with one or more indentations having a shape configured to receive the cushion. A magnet disposed proximate the indentation is oriented to attract the magnet within the cushion when the cushion is placed in the indentation to retain the cushion therein.

15 Claims, 3 Drawing Sheets

(56) References Cited

U.S. PATENT DOCUMENTS

| | | | | |
|---|---|---|---|---|
| 7,591,034 B2* | 9/2009 | Kramer | ................... | A61G 7/05 5/425 |
| 7,788,747 B2* | 9/2010 | Kramer | ................... | A61G 7/05 5/428 |
| 9,254,046 B1* | 2/2016 | Arenstein | ............. | A47C 21/022 |
| 9,254,179 B2* | 2/2016 | Limoni | ............... | A61B 19/26 |
| 2003/0093860 A1* | 5/2003 | Kramer | ................... | A61G 7/05 5/600 |
| 2005/0166322 A1* | 8/2005 | Kramer | ................... | A61G 7/05 5/430 |
| 2007/0180617 A1* | 8/2007 | Kramer | ................... | A61G 7/05 5/425 |
| 2010/0005589 A1* | 1/2010 | Kramer | ................... | A61G 7/05 5/428 |
| 2012/0233777 A1* | 9/2012 | Hare | ................... | A47C 21/022 5/498 |
| 2013/0042412 A1* | 2/2013 | Shih | ....................... | A47C 20/04 5/693 |
| 2013/0074269 A1* | 3/2013 | Phillips, II | ............ | A61F 5/0193 5/648 |
| 2014/0182060 A1* | 7/2014 | Mikkelsen | ........... | A47C 21/026 5/400 |
| 2015/0297302 A1* | 10/2015 | Limoni | .................. | A61B 19/26 248/510 |
| 2015/0374136 A1* | 12/2015 | Mikkelsen | ........... | A47C 21/026 5/411 |
| 2016/0228073 A1* | 8/2016 | Pruyne | ................... | A61B 6/032 |
| 2017/0105563 A1* | 4/2017 | Dawson | ............ | A47G 27/0293 |
| 2018/0098653 A1* | 4/2018 | Pinchuk | ............. | A47G 19/2261 |
| 2018/0125259 A1* | 5/2018 | Peterson | ............. | A47C 19/025 |
| 2018/0125260 A1* | 5/2018 | Peterson | ............. | A47C 31/003 |
| 2018/0202602 A1* | 7/2018 | Conti | .................... | A47G 23/02 |

* cited by examiner

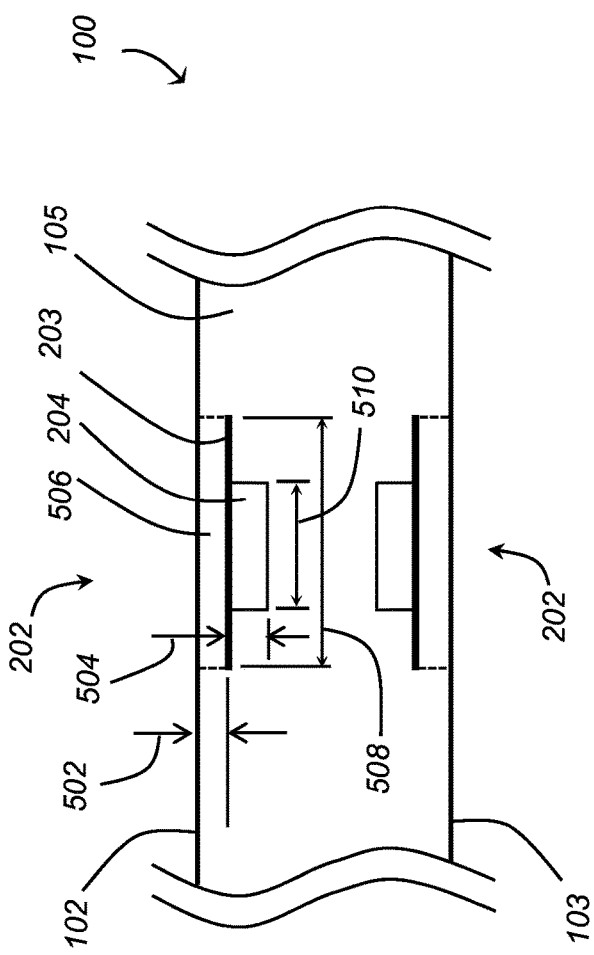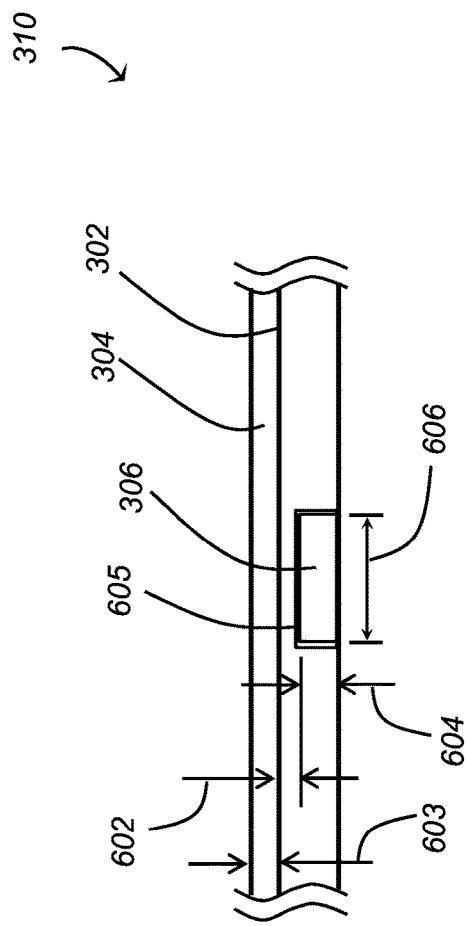

CUSHION RETAINER

CROSS REFERENCE TO RELATED APPLICATIONS

This application claims priority to U.S. Patent Application Ser. No. 62/112,190, filed Feb. 5, 2015, in the name of Pruyne, and entitled CUSHION RETAINER.

This application is related in certain respects to U.S. patent application Ser. No. 14/048,599, filed Oct. 8, 2013, in the name of Litzenberger et al., and entitled EXTREMITY IMAGING APPARATUS FOR CONE BEAM COMPUTED TOMOGRAPHY which is incorporated herein by reference in its entirety.

BACKGROUND OF THE INVENTION

The subject matter disclosed herein relates to cushions or padding for use with medical diagnostic equipment. In particular, to a diagnostic device having padding disposed thereon for purposes of patient comfort.

Oftentimes, medical diagnostic examination requires patients to come into contact with medical equipment. Hard surfaces and edges may cause patient pain or discomfort, in particular, if the contact is prolonged or requires significant pressure as between the equipment and patient anatomy. Such contact may occur when a patient must present their full or partial body weight against a medical apparatus. Multi-use medical devices may not always require that padding or cushioning be present, and such items may even present an obstruction for certain examination procedures. It would be advantageous for padding to be easily and quickly removed from and replaced on medical diagnostic equipment as needed.

The discussion above is merely provided for general background information and is not intended to be used as an aid in determining the scope of the claimed subject matter.

BRIEF DESCRIPTION OF THE INVENTION

A cushion assembly comprises a magnet disposed therewithin proximate one or both of two major surfaces of the cushion assembly. A medical diagnostic device comprises a contact surface wherein a part of a patient's body may contact the diagnostic device. The contact surface may be configured with one or more indentations having a shape configured to receive the cushion. A magnet disposed in the diagnostic device proximate the indentation is oriented to attract the magnet within the cushion, when the cushion is placed in the indentation, to retain the cushion. An advantage that may be realized in the practice of some disclosed embodiments of the cushion retainer assembly is a simplified removal and placement of the cushion for medical examinations as needed.

In one embodiment, a cushion retainer assembly includes a cushion having two major opposing surfaces. A first magnet is disposed within the cushion proximate one or more of the two major surfaces. A medical diagnostic device includes a corresponding indentation on a contact surface area wherein a part of a patient's body may contact the diagnostic device during certain procedures. The contact surface is configured with one or more indentations shaped to receive the cushion. A second magnet disposed proximate a surface of the indentation is oriented to attract the first magnet when the cushion is placed in the indentation so as to retain the cushion therein.

In another embodiment, a medical diagnostic assembly includes a medical diagnostic device that may physically contact a patient. The diagnostic device has an indentation to receive a cushion and shaped similar to the cushion. A magnet beneath a surface of the indentation is oriented to attract a magnet in the cushion when the cushion is placed in the indentation.

In another embodiment, an assembly includes a cushion between about one and one-half inches to about three inches thick. Magnets are disposed within the cushion and are made from a rare earth material and are shaped as discs having a thickness of about ¼ inch. The cushion has counter bores to receive the magnets that are shaped substantially similar to a shape of the magnets.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. Although the drawings are not necessarily to scale, emphasis is generally placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a side cross sectional view of a portion of the exemplary cushion assembly of FIGS. 1-2; and FIG. 6 is a side cross sectional view of a portion of the exemplary medical diagnostic device of FIGS. 3-4.

DETAILED DESCRIPTION OF THE INVENTION

Figure 2:
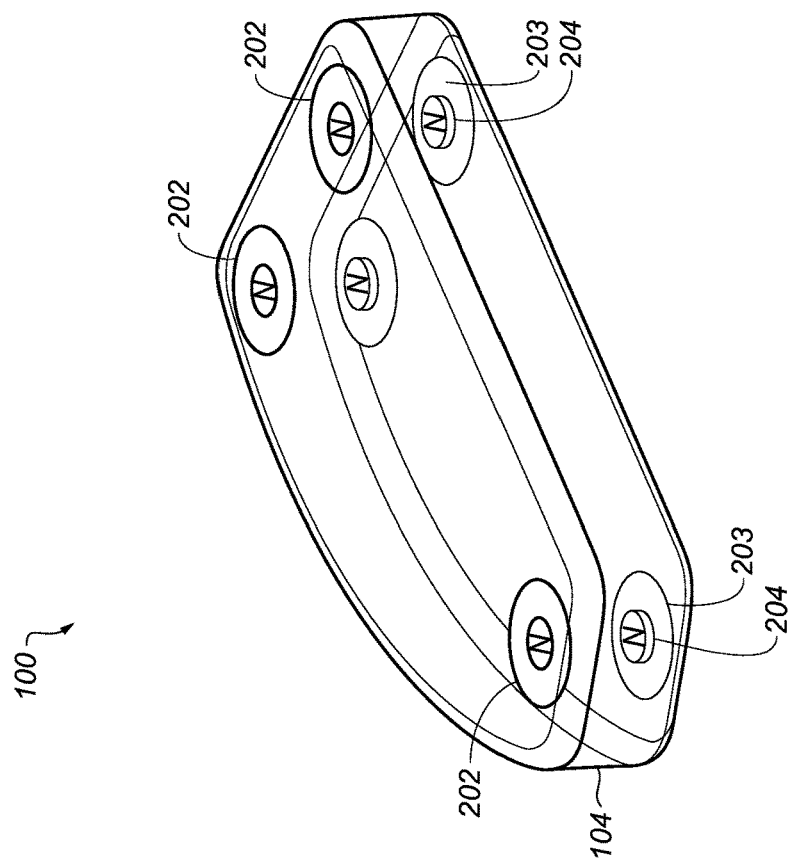
FIG. 2 is a transparent view of the exemplary cushion assembly of FIG. 1.
Figure 1:
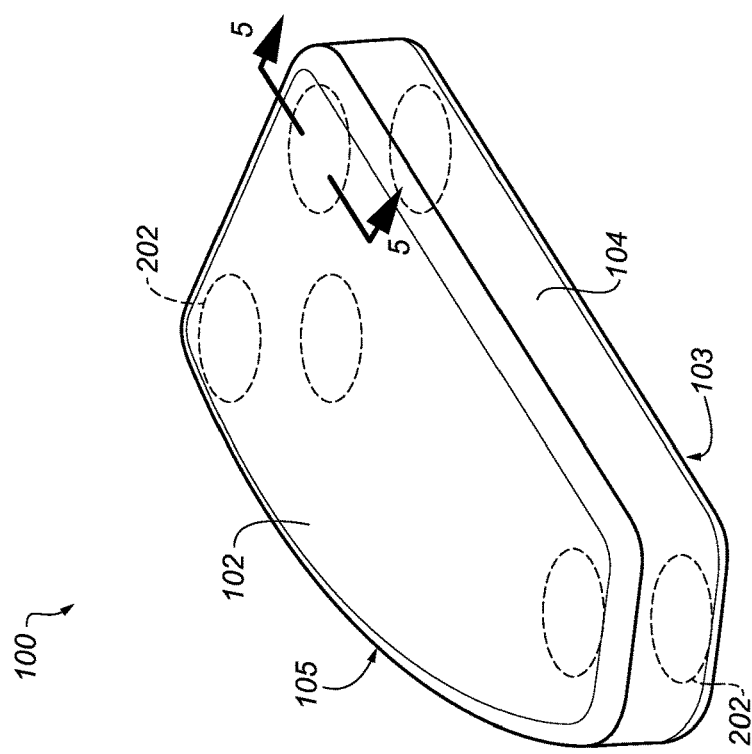
FIG. 1 is a perspective view of an exemplary cushion assembly.

FIGS. 1 and 2 each illustrate a perspective view of cushion assembly 100. FIG. 1 illustrates a general outline of the cushion assembly 100 and FIG. 2 illustrates a transparent view of the cushion assembly 100 which makes visible securing assemblies 202 within the cushion assembly 100 each including a magnet 204 and a force distribution disc 203. Not all instances of securing assemblies 202, magnets 204, and force distribution discs 203 are enumerated in the Figures, however, in the exemplary embodiment of FIGS. 1 and 2, the cushion assembly 100 comprises six securing assemblies 202 although the number may vary.

Each individual cushion assembly 100 comprises a substantially planar top surface 102 and a substantially planar bottom surface 103. The top and bottom surfaces 102, 103 may be said to be disposed on opposite sides of the cushion assembly 100 and comprise the largest planar surfaces of the cushion assembly 100. The cushion assembly 100 comprises substantially continuous side surfaces 104 continuously and integrally formed with the top and bottom surfaces 102, 103, and substantially perpendicular thereto. The side surfaces may form a corner where they meet the top and bottom surfaces or they may form a rounded edge. The bulk 105 of the cushion assembly 100 is fabricated from a flexible, spongy, relatively soft foam material that yields to pressure. In one embodiment, the bulk 105 of the cushion assembly 100 may comprise cross-linked closed cell ethyl vinyl acetate (EVA) foam at a density of about 2 lb/ft$^3$. The thickness of the cushion assembly 100, i.e., a distance between top and bottom surfaces 102, 103, may range from about one-half inch to about four inches, more preferably from about one and one-half inch to about three inches, and even more preferably about two and one-quarter inches to about two and three-quarter inches. The thickness of the cushion assembly 100 may vary depending on the density of the selected cushion material and on the intended medical diagnostic application. The general outline, or shape, of the cushion assembly 100 may vary and may be selected for various purposes, such as for fitting on a particular medical diagnostic device.

The magnet 204 of each securing assembly 202 may be disposed in the foam adjacent to the force distribution discs 203, or they may be attached to the force distribution discs 203 using a suitable adhesive, for example. In one embodiment, the magnets 204 may be formed in the shape of a disc of about one inch diameter and about ¼ inch thick, although the selected sizes may vary depending on particular applications and materials used, as desired. In one embodiment, the magnets 204 may be formed as rare earth magnets out of a material known in the art as N52 type. The force distribution discs 203, adjacent the magnets 204, may be fabricated as plastic discs, such as a polycarbonate material, semi-rigid in structure, having a diameter of about two inches and, if glued, they may be attached to the magnets 204 using Fast 77 spray adhesive made by the 3M Company, for example. A thickness of the force distribution discs may range from about 0.005 inch to about 0.025 inch, more preferably from about 0.010 inch to about 0.020 inch, and may vary somewhat depending on the rigidity or formulation of the thermoplastic material used.

The securing assemblies 202 may be placed in the EVA foam bulk 105 of the cushion assembly 100 during manufacture, such as during injection molding, for example, or they may be placed in counter bored openings 506 (FIG. 5) formed in the bulk 105 of the cushion material after molding. The counter bored openings 506 match the size of the magnet 204 and the force distribution disc 203, and may be back filled with foam or closed with a foam plug, for example, after placement of the securing assemblies 202 therein. The magnet 204 may be disposed on an inward facing side of the force distribution disc 203 (away from a major surface 102, 103) whereby the force distribution disc 203 faces the major surface 102, 103, of the cushion assembly 100 at a depth of about ¼ inch therefrom, for example. The surfaces 102-104 of the cushion assembly 100 may be colored, such as by spray painting, using a spray coated matte black low tack single coat paint, as an example. The magnets 204 may be disposed in the cushion assemblies 100 such that their north poles face the top surface 102 of the cushion assembly 100 and their south poles face the bottom surface 103 of the cushion assembly 100. Such orientations of the magnets 204 facilitate stacking the cushion assemblies 100 as the magnets 204 will assist in holding the cushion assemblies 100 in a stacked formation. The magnets 204 may be configured in various other orientations such that they cooperate with magnets placed in a medical diagnostic device and in other cushion assemblies 100.

Figure 4:
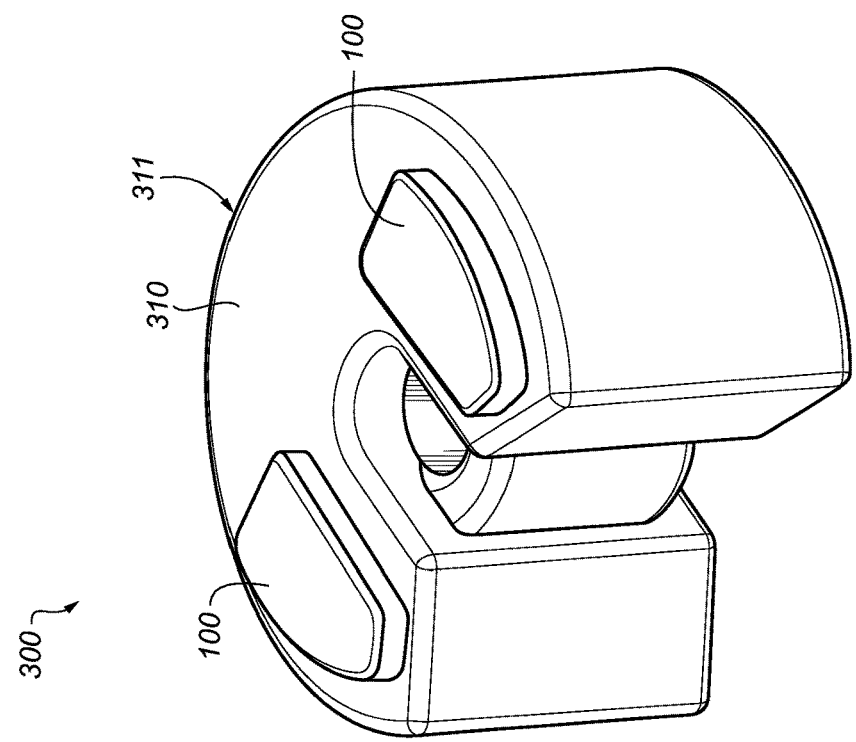
FIG. 4 is a perspective view of the exemplary medical diagnostic device of FIG. 3 having a plurality of the exemplary cushion assembly of FIGS. 1-2 disposed thereon.
Figure 3:
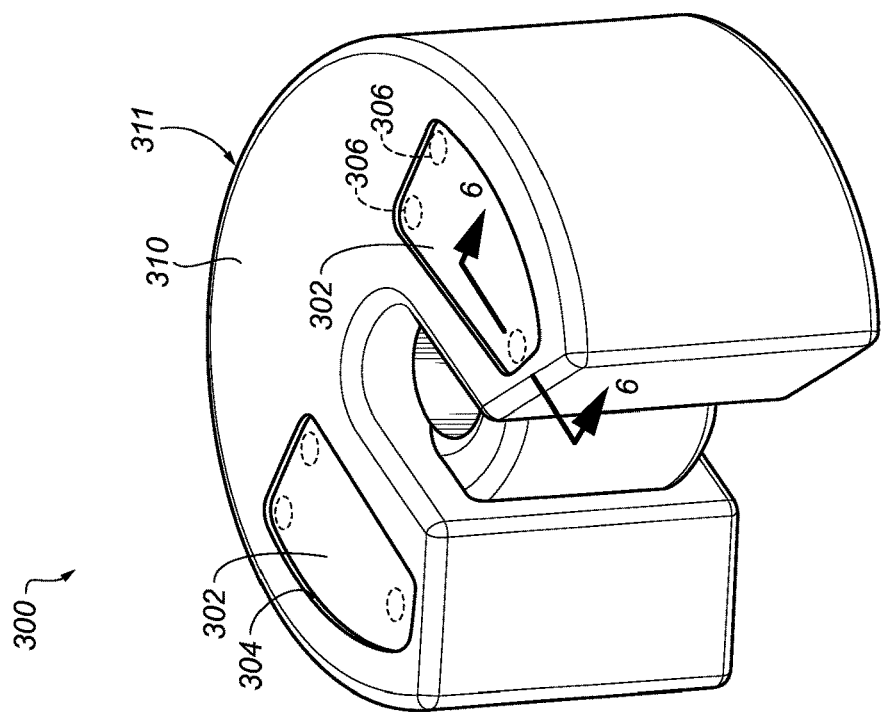
FIG. 3 is a perspective view of an exemplary medical diagnostic device having indentations, or recesses, in its housing to receive the exemplary cushion assembly of FIGS. 1-2.

FIGS. 3 and 4 illustrate a housing 310 of an exemplary medical diagnostic x-ray device 311 known as an Extremity Imager for Cone Beam Computed Tomography (CBCT), such as described in the US Patent Application identified above and incorporated by reference herein. In one embodiment, the housing 310 of the CBCT imager 311 includes indentations 302 formed in a surface thereof which, together with the cushion assembly 100, forms a cushion retainer assembly 300 of the present invention. These indentations 302 may be formed integrally in the housing 310 or they may comprise openings in the housing 310 that are fitted with a cover that provides the recess 302 for receiving the cushion assembly 100. The indentations 302, or depressions, are shaped to match the outline of the cushion assembly 100 such that placement of the cushion assembly 100 therein forms a mating fit (FIG. 4). The indentations 302 are formed at a depth, such as about ¼ inch, suitable to prevent unwanted sideways displacement of the cushion assembly 100 after placement of the cushion assembly 100 in the indentation 302. The sidewall 304 of the depression 302 preferably makes contact with a corner or sidewall 104 of the cushion assembly 100 to prevent such sideward displacement. Magnets 306 may be placed below a surface of the recessed portion 302 of the housing 310 such that they attract the magnets 204 in the cushion assemblies 100, i.e., the north poles of the magnets 306 face upward toward the recessed portion 302 and the south poles of the cushion assembly 100 magnets 204. The configuration of the CBCT imager 311, as an exemplary medical diagnostic device, together with the cushion assembly 100 facilitate easy removal and replacement of cushion assemblies 100 as needed for diagnostic procedures using the CBCT imager 311.

FIG. 5 illustrates a cross sectional view of the cushion assembly 100 to better illustrate dimensions of the securing assemblies 202 in relation to the cushion assembly 100 as described herein. As shown, one of the securing assemblies 202 is disposed proximate the top surface 102 of the cushion assembly 100 and comprises a magnet 204 adjacent a force distribution disc 203 disposed in a counter bore 506 formed in the bulk 105 of a foam based cushion assembly 100. In one embodiment, a diameter 510 of the magnet 204 may be about 1 inch and the diameter 508 of the force distribution disc 203 may be about 2 inches. In one embodiment, a thickness 504 of the magnet 204 may be about ¼ inch and a depth 502 from the top surface 102 to the force distribution disc 203 may also be about ¼ inch. As previously described herein, the depth 502, formed by a counter bore in the top surface 102, may be back filled with foam or closed with a foam plug, for example, after placement of the securing assembly 202 therein. The dimensions of the securing assembly 202 that is placed proximate the bottom surface 103 of the cushion assembly 100 and its position within the cushion assembly 100 may be similar to the dimensions just described. The dimensions and distances described here may vary without departing from the scope of the present invention.

FIG. 6 illustrates a cross sectional view of the top surface of the housing 310 having an indentation 302, or cover as explained above, formed therein. As shown, indentation 302 may comprise a sidewall 304 having a depth 603 of about ⅜ inch. In one embodiment, a magnet 306, having a disc shape, for example, may be disposed at a distance 602 of about 0.02 inches to about 0.06 inches, preferably about 0.04 inches, from a surface of the indentation 302. In one embodiment, a diameter 606 of the magnet 306 may be about 1 inch and a thickness 604 of the magnet 306 may be about ¼ inch. In one embodiment, the magnet 306 may be affixed, such as by an adhesive, into a counterbored recess 605, slightly larger than the magnet 306, formed in the bottom side of the cover or housing 310. In this embodiment, consistent with the orientations of the magnets 204 in the cushion assembly 100 as described above, the magnet's upper (or top) surface, in the perspective shown in FIG. 6, comprises a magnetic north pole, opposite the bottom surface south pole. The dimensions and distances described herein may vary without departing from the scope of the present invention.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An assembly for use with a medical apparatus, the assembly comprising:
    a cushion made from a soft material that is configured to yield to pressure from a full or partial body weight of a patient against the cushion, the cushion comprising top and bottom opposing surfaces and a continuous sidewall extending between the top and bottom opposing surfaces, the bottom opposing surface comprising a planar bottom surface;
    a plurality of bottom magnets disposed within the cushion proximate the planar bottom surface of the cushion; and
    a plurality of bottom force distribution members each disposed within the cushion spaced from the planar bottom surface of the cushion between one of the bottom magnets and the planar bottom surface of the cushion, and each adjacent said one of the bottom magnets,
    wherein the plurality of bottom force distribution members are each wider than a width of the adjacent bottom magnet such that no edge of any bottom magnet extends beyond an edge of an adjacent bottom force distribution member in a direction toward the sidewall.

2. The assembly of claim 1, wherein the cushion further comprises cross linked closed cell ethyl vinyl acetate foam at a density of about 2 lb/ft$^3$.

3. The assembly of claim 2, wherein the cushion has a thickness between about one half inch to about four inches.

4. The assembly of claim 3, wherein the cushion has a thickness more preferably from about one and one-half inch to about three inches.

5. The assembly of claim 1, further comprising a plurality of bottom counter bores in the planar bottom surface of the cushion, the bottom counter bores each having a first bottom counter bore opening to receive one of the bottom force distribution members, a shape of the first bottom counter bore openings each matching a shape of the bottom force distribution member received therein, the bottom counter bores each further having a corresponding second bottom counter bore opening smaller than the corresponding first bottom counter bore opening and disposed near a center of the corresponding first bottom counter bore opening, the second bottom counter bore openings each to receive one of the plurality of bottom magnets adjacent a bottom force distribution member in the corresponding first bottom counter bore opening, a shape of the second bottom counter bore openings each matching a shape of the bottom magnet received therein.

6. The assembly of claim 5, wherein the bottom force distribution members are each attached to one of the bottom magnets.

7. The assembly of claim 5, further comprising:
    a plurality of top magnets disposed within the cushion proximate the top surface of the cushion; and
    a plurality of top force distribution members each disposed within the cushion spaced from the top surface of the cushion between one of the top magnets and the top surface of the cushion, and each adjacent said one of the top magnets,
    wherein the plurality of top force distribution members are each wider than a width of the adjacent top magnet such that no edge of any top magnet extends beyond an edge of an adjacent top force distribution member in a direction toward the sidewall.

8. The assembly of claim 7, further comprising a plurality of top counter bores in the top surface of the cushion, the top counter bores each having a first top counter bore opening to receive one of the top force distribution members, a shape of the first top counter bore openings each matching a shape of the top force distribution member received therein, the top counter bore openings each further having a corresponding second top counter bore opening smaller than the corresponding first top counter bore opening and disposed near a center of the corresponding first top counter bore opening, the second top counter bore openings each to receive one of the plurality of top magnets adjacent a top force distribution member in the corresponding first top counter bore opening, a shape of the second top counter bore openings each matching a shape of the top magnet received therein.

9. The assembly of claim 7, wherein a magnetic pole of the bottom magnets facing the bottom surface of the cushion is opposite to the magnetic pole of the top magnets facing the top surface of the cushion.

10. The assembly of claim 1, wherein the medical apparatus comprises an indentation having a planar apparatus bottom surface comprising a shape substantially matching a shape of the planar bottom surface of the cushion.

11. The assembly of claim 10, further comprising a plurality of apparatus magnets disposed beneath the planar apparatus bottom surface of the indentation, the plurality of apparatus magnets each positioned to align with one of the bottom magnets in the cushion and each oriented to attract said one of the bottom magnets in the cushion when the cushion is placed in the indentation.

12. A medical diagnostic assembly comprising:
a medical diagnostic device configured to physically contact a patient, the diagnostic device comprising:
an indentation to receive a cushion, the indentation having a planar indentation bottom surface, a shape of the planar indentation bottom surface substantially matching a shape of the cushion; and
a plurality of medical device magnets disposed beneath the planar indentation bottom surface; and
the cushion comprising:
a soft material that is configured to yield to pressure from a full or partial body weight of a patient against the cushion;
two opposing surfaces comprising a top surface and a planar bottom surface;
a plurality of cushion magnets disposed within the cushion proximate the bottom surface thereof; and
a plurality of force distribution members each disposed within the cushion spaced from the planar bottom surface of the cushion between one of the cushion magnets and the bottom surface of the cushion, and each adjacent said one of the cushion magnets,
wherein the plurality of cushion magnets are each aligned with a position of one of the medical device magnets and oriented to attract said one of the medical device magnets when the cushion is placed in the indentation.

13. The medical diagnostic assembly of claim 12, wherein the cushion further comprises cross linked closed cell ethyl vinyl acetate foam at a density of about 2 lb/ft$^3$, the cushion has a thickness between about one half inch to about four inches, and wherein the medical device magnets and the cushion magnets each comprise a rare earth material and is shaped as a disc having a thickness of about ¼ inch and a diameter of about one inch.

14. The medical diagnostic assembly of claim 13, wherein the cushion comprises a plurality of counter bores in the planar bottom surface thereof, the counter bores each having a first counter bore opening to receive one of the force distribution members, a shape of the first counter bore openings each matching a shape of the force distribution member received therein, the counter bores each having a corresponding second counter bore opening smaller than the corresponding first counter bore opening and disposed near a center of the corresponding first counter bore opening, the second counter bore openings to receive one of the plurality of cushion magnets adjacent the force distribution member in the corresponding first counter bore opening, a shape of the second counter bore openings each matching a shape of the cushion magnet received therein.

15. The medical diagnostic assembly of claim 14, wherein the force distribution members each comprise polycarbonate plastic, has a thickness of about 0.010 inch to about 0.020 inch, and is disposed about ¼ inch from said planar bottom surface.

* * * * *